US010459835B1

United States Patent
George et al.

(10) Patent No.: US 10,459,835 B1
(45) Date of Patent: Oct. 29, 2019

(54) SYSTEM AND METHOD FOR CONTROLLING QUALITY OF PERFORMANCE OF DIGITAL APPLICATIONS

(71) Applicant: Accenture Global Solutions Limited, Dublin (IE)

(72) Inventors: Reuben Rajan George, Bangalore (IN); Muralikrishna Neelakandam Jayagopal, Chennai (IN); Mahender Rajpurohit, Aylesbury (GB); Muralidhar Yalla, Bangalore (IN); Venugopal Ramakrishnan, Aldershot (GB)

(73) Assignee: Accenture Global Solutions Limited, Dublin (IE)

( * ) Notice: Subject to any disclaimer, the term of this patent is extended or adjusted under 35 U.S.C. 154(b) by 0 days.

(21) Appl. No.: 16/230,653

(22) Filed: Dec. 21, 2018

(30) Foreign Application Priority Data

Aug. 29, 2018 (IN) .............................. 201841032397

(51) Int. Cl.
*G06F 11/00* (2006.01)
*G06F 11/36* (2006.01)
(Continued)

(52) U.S. Cl.
CPC ........ *G06F 11/3692* (2013.01); *G06F 8/4435* (2013.01); *G06F 11/0793* (2013.01); *G06F 16/906* (2019.01); *G06N 20/00* (2019.01)

(58) Field of Classification Search
CPC . G06F 11/3692; G06F 11/0793; G06F 8/4435
See application file for complete search history.

(56) References Cited

U.S. PATENT DOCUMENTS 7,020,697 B1   3/2006  Goodman et al.
9,753,731 B1 *  9/2017  Puzovic .............. G06F 9/30181
(Continued)

OTHER PUBLICATIONS

Extended European Search Report dated Aug. 5, 2019 for European Patent Application No. 19151018.9.
(Continued)

*Primary Examiner* — Philip Guyton
(74) *Attorney, Agent, or Firm* — Plumsea Law Group, LLC

(57) ABSTRACT

A system and method for controlling quality of performance of a digital application is disclosed. Performance data representing test results of a requested performance test on the application is obtained. A performance metric is optimized by analyzing the performance data and classifying analysis results of the analyzing into multiple categories, including an immediate remediation category. An automated modification is initiated based on a first analysis result classified into the immediate remediation category. An automated verification performance test determines a measure of improvement in performance of the application based on the modification by comparing a first verification result of a first performance test without the automated modification with a second verification result of a second performance test of the digital application with the automated front end modification. The digital application with the automated modification may be deployed based on a result of the automated verification performance test.

20 Claims, 5 Drawing Sheets

(51) Int. Cl.
*G06F 8/41* (2018.01)
*G06N 20/00* (2019.01)
*G06F 16/906* (2019.01)
*G06F 11/07* (2006.01)

(56) References Cited

U.S. PATENT DOCUMENTS

| | | | | |
|---|---|---|---|---|
| 2009/0125886 A1* | 5/2009 | Owens, II | ............ | G06F 11/3688 717/124 |
| 2013/0080760 A1* | 3/2013 | Li | ................ | G06F 11/3409 713/100 |
| 2014/0281732 A1* | 9/2014 | Elias | ................ | G06F 11/3692 714/38.1 |
| 2015/0347282 A1* | 12/2015 | Wingfors | ............ | G06F 11/3688 717/125 |
| 2018/0060223 A1* | 3/2018 | Cheung | ............ | G06F 11/3692 |
| 2018/0253372 A1* | 9/2018 | Colaiacomo | ........ | G06F 11/3692 |

OTHER PUBLICATIONS

Mikulin D. et al.: "Incremental linking on 1-15 HP-UX", Proceedings of the Workshop on Industrial Experiences With Systems Software, Jan. 1, 2000, pp. 47-56, XP002473613.

* cited by examiner

SYSTEM AND METHOD FOR CONTROLLING QUALITY OF PERFORMANCE OF DIGITAL APPLICATIONS

CROSS-REFERENCE TO RELATED APPLICATION

This application claims priority to Indian Provisional Patent Application Number 201841032397 filed on Aug. 29, 2018, the disclosure of which is hereby incorporated by reference.

TECHNICAL FIELD

The present disclosure generally relates to controlling quality of performance of digital applications. More specifically, the present disclosure generally relates to a system and method for controlling quality of performance of web applications and/or mobile applications. Even more specifically, the present disclosure generally relates to a system and method for automatically determining remedial modifications based on testing the performance of a digital application, automatically modifying the digital application based on an analysis result indicating an immediate modification to optimize performance of the application, and testing to verify an improvement in performance for the modified application.

BACKGROUND

Digital applications are used widely for numerous scenarios in which users expect high quality performance. In many scenarios, there is little tolerance for marginal performance in execution of various applications. For example, a medical professional may need computerized assistance while treating patients remotely. For example, if an inefficient computing process causes a transition from a first page (e.g., page A) to a second page (e.g., page B) in results of a search for proper treatment of a stroke to take several seconds, a patient's health (or life) may literally be at risk due to reduced quality of performance of the application. As another example, military personnel may need computerized assistance via a mobile device while out in the field, under attack. For example, if a soldier needs to be authenticated via a login to receive information regarding enemy territory, in an area where he/she normally does not log in on his/her mobile device, and simple login screens are distorted such that the soldier is unable to decipher instructions for authentication, then the soldier's life may be in danger.

As yet another example, many applications such as connected car applications and self-driving car applications may require low latency performance. Further, per second delay in retail applications (e.g., AMAZON, BEST BUY, etc.) may result in loss of revenue and loss in conversions. In this context, digital applications may include web applications and mobile applications. For example, customers may use such digital applications to communicate with numerous types of systems in a backend, including, at least, conversational bots (e.g., for customer feedback), Internet of things (IoT) solutions (e.g., home automation), and domain related web services (e.g., finance, retail, hospitality (hotels, travel)).

Testing for quality performance of digital applications traditionally occurs on a server (e.g., on a backend), and may not account for variations in locale or operating conditions. Further, traditional testing may not analyze front end loading performance in realistic execution conditions, to determine potential optimizations that may aid in performance of the digital application. Further, traditional testing may not provide any recommendations for front end performance improvements, and may only collect timing measurements using javascripts running on a page. Additionally, traditional remedial actions may require manual code modifications, with tedious testing before deploying or re-deploying the modified application. Even further, it may be difficult, or even impossible, to accurately determine modifications to the design of an application, that may improve performance of the application.

There is a need in the art for a system and method that addresses the shortcomings discussed above.

SUMMARY

A system and method for controlling quality of performance of a digital application is disclosed. The system and method solves the problems discussed above by detecting performance issues and classifying potential modifications, as well as automatically modifying the digital application, and validating that the modification improves the performance of the digital application. By completing these tasks, the system can automatically remediate quality of performance issues, for modifications that are classified into an immediate remediation category. For example, front end loading issues may be automatically remediated. The system may also store historical performance data, so that future modifications may be tested against performance measures of past versions of the digital application, to ensure that quality of performance is improved by the modifications. Furthermore, the quality of performance of the digital application may be tested by bots, on an actual device, the bots trained by machine learning techniques, to test the digital application without scripts, under simulated conditions that may affect the quality of performance of the digital application (e.g., network, CPU, memory, battery conditions of the device).

For example, the system and method, as part of testing the digital application, may run the web/mobile application on an actual browser and device, and may collect user experience data (e.g., timing metrics and performance heuristics) and may perform an analysis on the impact of front end logic on performance delays.

As another example, some traditional tools may perform bot-driven user interface (UI) automation of performance testing but may not provide performance improvement recommendations or perform optimizations, in contrast to the systems and methods discussed herein. As another example, some traditional tools may perform load testing of mobile and web applications but may not provide front end performance measurements and recommendations to improve page rendering and speed. In contrast, systems and methods discussed herein may augment load testing tools by running alongside load test executions and generate front end performance timings and recommendations during a load test.

In one aspect, the disclosure provides a method of controlling quality of performance of a digital application. The method may include obtaining first performance data representing first test results of a requested performance test on the digital application. At least a portion of the digital application may be obtained. A performance metric of the digital application may be optimized by analyzing the first performance data and classifying analysis results of the analyzing into a plurality of categories, the plurality of categories including an immediate remediation category, and initiating an automated modification of the digital application based on a first analysis result classified into the immediate remediation category. An automated verification performance test may be initiated to determine a measure of improvement in performance of the digital application based on the modification of the digital application by comparing a first verification result of a first performance test of the digital application without the automated modification with a second verification result of a second performance test of the digital application with the automated front end modification. The digital application with the automated modification may be deployed based on a result of the automated verification performance test.

In another aspect, the disclosure provides a non-transitory computer-readable medium storing software comprising instructions that are executable by one or more device processors to control quality of performance of a digital application by obtaining first performance data representing first test results of a requested performance test on the digital application. At least a portion of the digital application may be obtained. A performance metric of the digital application may be optimized by analyzing the first performance data and classifying analysis results of the analyzing into a plurality of categories, the plurality of categories including an immediate remediation category, and initiating an automated modification of the digital application based on a first analysis result classified into the immediate remediation category. An automated verification performance test may be initiated to determine a measure of improvement in performance of the digital application based on the modification of the digital application by comparing a first verification result of a first performance test of the digital application without the automated modification with a second verification result of a second performance test of the digital application with the automated front end modification. The digital application with the automated modification may be deployed based on a result of the automated verification performance test.

In another aspect, the disclosure provides a system for controlling quality of performance of a digital application, the system comprising a device processor and a non-transitory computer readable medium storing instructions that are executable by the device processor to obtain first performance data representing first test results of a requested performance test on the digital application and obtain at least a portion of the digital application. A performance metric of the digital application may be optimized by analyzing the first performance data and classifying analysis results of the analyzing into a plurality of categories, the plurality of categories including an immediate remediation category, and initiating an automated modification of the digital application based on a first analysis result classified into the immediate remediation category. An automated verification performance test may be initiated to determine a measure of improvement in performance of the digital application based on the modification of the digital application by comparing a first verification result of a first performance test of the digital application without the automated modification with a second verification result of a second performance test of the digital application with the automated front end modification. The digital application with the automated modification may be deployed based on a result of the automated verification performance test.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

While various embodiments are described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted.

This disclosure includes and contemplates combinations with features and elements known to the average artisan in the art. The embodiments, features, and elements that have been disclosed may also be combined with any conventional features or elements to form a distinct invention as defined by the claims. Any feature or element of any embodiment may also be combined with features or elements from other inventions to form another distinct invention as defined by the claims. Therefore, it will be understood that any of the features shown and/or discussed in the present disclosure may be implemented singularly or in any suitable combination. Accordingly, the embodiments are not to be restricted except in light of the attached claims and their equivalents. Also, various modifications and changes may be made within the scope of the attached claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

DESCRIPTION OF EMBODIMENTS

A system and method for controlling quality of performance of a digital application is disclosed. As discussed in more detail below, the system and method can be used for web applications and mobile applications. The system and method detects quality of performance issues and classifies recommended modifications to remediate the quality of performance issues, as well as automatically modifying the digital application, testing the modified application to ensure improved performance, and deploying the modified application, for recommended modifications to code of the digital application that are categorized as immediate modifications.

Figure 1:
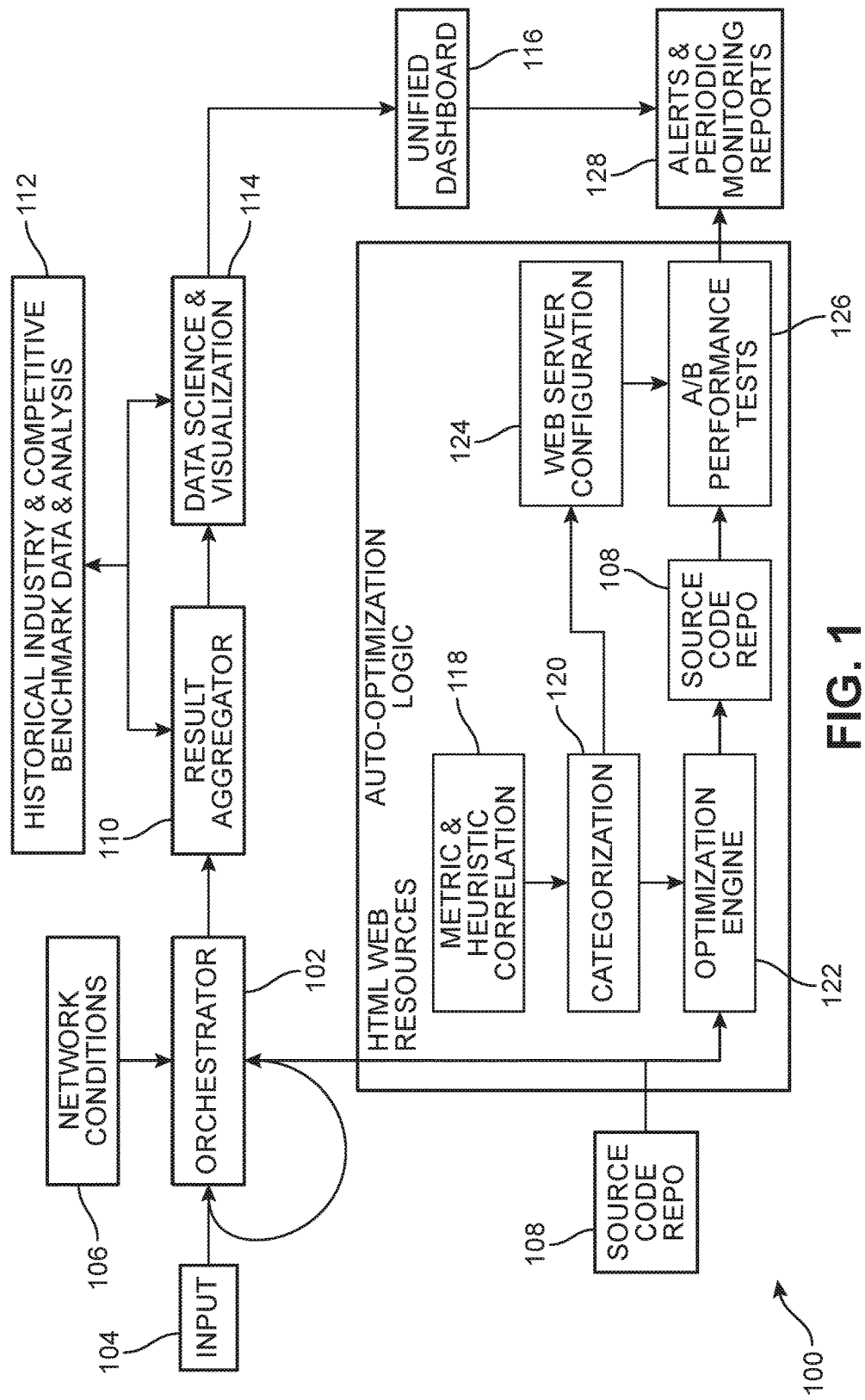
FIG. 1 is a schematic diagram of an embodiment of a system for controlling quality of performance of a digital application.

For example, FIG. 1 shows an example embodiment of a system 100 for controlling quality of performance of a digital application. As shown in FIG. 1, an orchestrator 102 receives input 104 for processing by the system 100. For example, orchestrator 102 may control execution of various components of system 100. In some embodiments, orchestrator 102 may control distributed processing, in parallel, of various modules/components of system 100. Associated systems for communicating with system 100 may include one or more user devices, such as a computer, a server, a database, and a network. A component running on a server could communicate with a user over a network. In some embodiments, the network may be a wide area network ("WAN"), e.g., the Internet. In other embodiments, the network may be a local area network ("LAN"). For example, in a more remote location far from a metropolitan area, the Internet may not be available. In yet other embodiments, the network may be a combination of a WAN and a LAN.

The user device may be a computing device used by a user for communicating with system 100. A computing device may include a tablet computer, a smartphone, a laptop computer, a desktop computer, or another type of computing device. The user device may include a display that provides an interface for the user to input and/or view information. For example, a user could interact with system 100 using a program run on a laptop computer, such as a text-based chat program, a voice-based communication program, and/or a video-based communication program. Alternatively, in some cases, the user device could be a telephone (e.g., a landline, cell phone, etc.).

One or more resources of system 100 may be run on one or more servers. Each server may be a single computer, the partial computing resources of a single computer, a plurality of computers communicating with one another, or a network of remote servers (e.g., cloud). The one or more servers can house local databases and/or communicate with one or more external databases.

Application testing may be performed on demand, via scheduled testing, or via periodic monitoring. As shown in FIG. 1, network conditions 106 may include a library to simulate network conditions in testing. For example, network conditions may include cable, wifi, 3G, 2G, or 4G network conditions. For example, other network conditions may include load conditions. A source code repository 108 may store source code of the digital applications, which may be input to system 100.

A result aggregator 110 may obtain the test results, parse, and grade the data, which may be input in multiple different formats, to output data in a uniform format, or as normalized data. For example, result aggregator 110 may determine performance issues that affect the most pages of the digital application. Historical and competitive benchmark data and analysis module 112 may provide historical data for comparison of performance with current versions of the digital application. For example, performance data may be stored as it is processed, for future use in testing applications. In some embodiments, performance data relating to a peer, or a competitor, of a user may be stored and provided for benchmarking against the peer or competitor. A data science and visualization module 114 may receive the aggregated data and benchmark data and provide that to a unified dashboard 116 for consumption by a user. For example, unified dashboard 116 may provide a display of analysis results and/or recommendation.

A metric and heuristic correlation module 118 may obtain test result data and correlate performance issues with particular portions of code of the digital application, for use in code modification. A categorization module 120 may categorize and prioritize recommendations for remediation of detected/determined performance issues of the digital application. For example, the categorization module 120 may determine recommendations based on at least three categories: (1) an immediate fix category, for recommended modifications that may be performed automatically, immediately (e.g., modifications to code of the digital application); (2) a short term fix category, for recommended modifications that may require modifications to the design of the digital application; and (3) a long term fix category, which may require a different methodology in the design of the digital application. For example, as an immediate fix, categorization module 120 may provide a list of one or more possible frontend fixes to an optimization engine 122 that may automatically remediate the performance issues by initiating a recommended modification. For example, frontend fixes may be initiated to remediate performance issues relating to loading pages, or to removing unused code from the digital application, or to use different compression techniques for images and/or text.

A web server configuration module 124 may process recommended modifications to the server. For example, an administrator may be alerted to the recommended modifications, and permissions to modify the server may be granted, so that the server configuration may be modified to optimize performance quality. For example, modifications may involve htaccess, http compression, redirects, caching, etc.

As shown in FIG. 1, the source code repository 108 may provide an input to a test module 126 for NB performance tests to validate improvements to performance quality as a result of making modifications to the digital application. For example, the digital application may be tested with and without the recommended modification, to verify that the modifications actually improve performance quality. The modified and tested digital application may then be deployed (or productionized). Additionally, alerts and periodic monitoring reports 128 may be provided, for example, via the unified dashboard 116.

As discussed further herein, system 100 may initiate performance tests on the digital application in script-less mode, driven by artificial intelligence (AI) driven bots. In some embodiments, the performance tests may emulate system behavior during a spike in user volume and evaluate the impact on user experience (as part of the testing of quality of performance). Additionally, the performance of the digital application may be compared with peers/competitors/industry groups, as well as cross browser/device/network/geographical coverage comparisons.

In some embodiments, a user is advantageously provided with high visibility on how their applications perform, in comparison with peers in the industry. Further, the impact of technology used may be correlated with performance. For example, the performance testing and analysis may show that lazy loading logic employed by Peer A serves five search results faster than pagination logic employed by Peer B to serve three search results.

In some embodiments, recommendations or fixes may be intelligently categorized (e.g., based on scope and/or complexity) and test results may be published to developers and performance engineers, for example, by automatically segregating issues that need an immediate fix, issues that need short term planning (e.g., extensive server configurational change), and issues that need long-term planning (e.g., changes in design and/or methodology of design).

In some embodiments, development assets may be optimized to comply with performance test recommendations and best practices. For example, image and/or text data may be optimized (e.g., compressed/minified/removed) as soon as performance audits are completed after a code push.

In some embodiments, performance testers and developers may be provided with tools to compare performance test results with past test results (e.g., benchmarks) and industry peers and to identify page components (e.g., HTML, Android/iOS code, JavaScript (JS), Cascading Style Sheets (CSS), images, fonts, text) that impact variance in quality of performance.

In some embodiments, the impact of recommendations on actual performance improvements may be scientifically validated. For example, NB tests may be run on optimized code and validation may indicate that the fixes actually improved the performance of the digital application, and the variance of improvement may be measured and provided to users, as well as to a repository for historical data.

In some embodiments, performance tests for testing load stress may be made more insightful by determining an impact of the technology used for implementing the application, on the quality of performance of the application (e.g., rather than simply displaying load testing and server performance diagnostic results). For example, using industry benchmarked data may provide an insight that lazy loading logic employed by Peer A shows they serve 5 search results faster than pagination logic used by Peer B to serve 3 search results. As another example, the performance tests may be made more insightful by providing access to domain specific projects where the approach/tool is already executed (historical), which, for example, may suggest performance of an application employing a technology for serving search results compared to other projects already executed that have employed another technology.

In some embodiments, performance testing and optimization is completely automated, with no human (or other user) intervention. In some embodiments, performance issues may be automatically categorized, based on severity and priority (e.g., issues that need immediate fix and the impact of such fixes).

Figure 2:
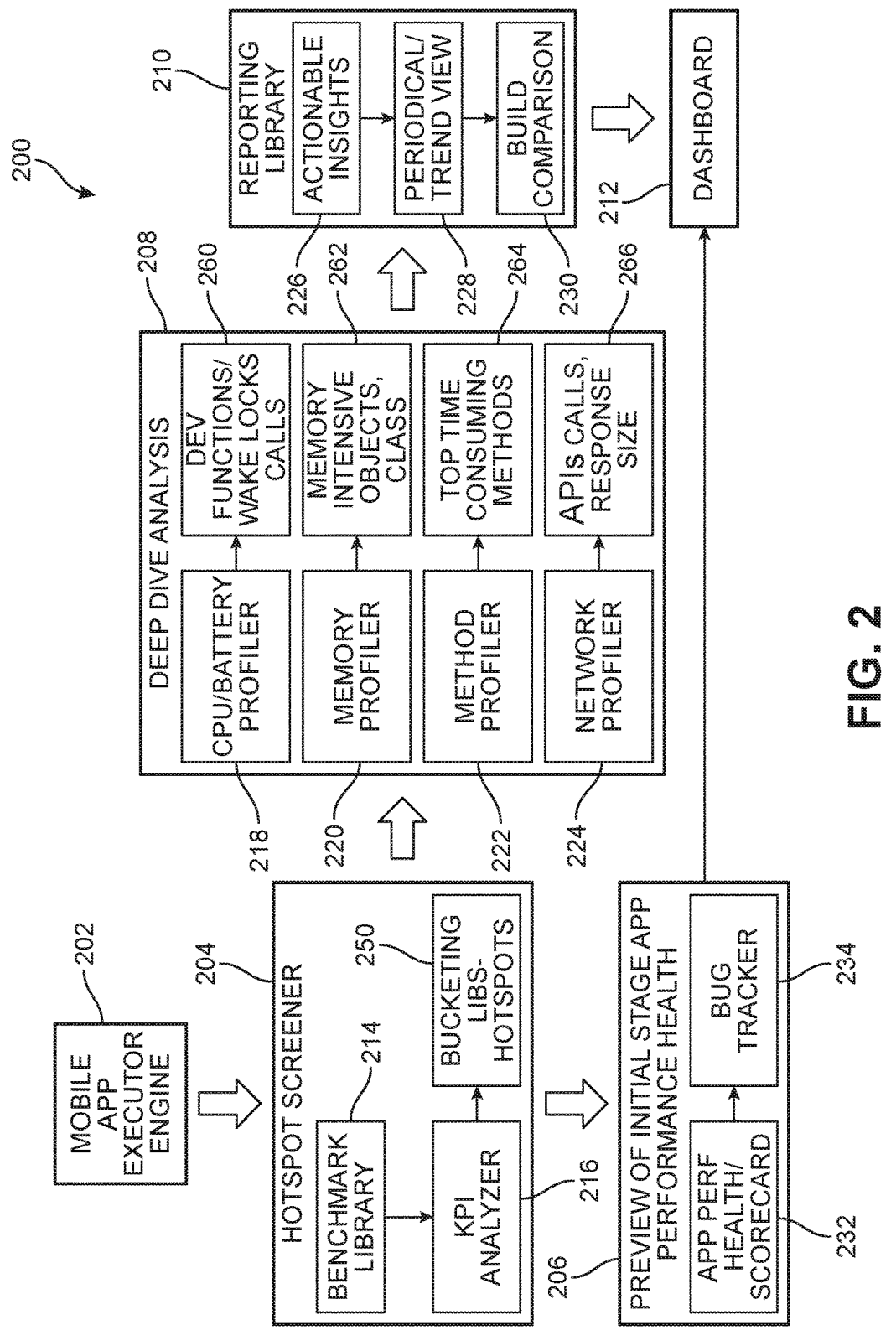
FIG. 2 is a schematic diagram of an embodiment of a system for controlling quality of performance of a digital application.

FIG. 2 is a schematic diagram of an embodiment of a system for controlling quality of performance of a digital application. As shown in FIG. 2, a mobile application performance component 200 is configured to measure mobile application performance in a real device under varied cellular network conditions. As shown in FIG. 2, application performance component 200 includes a mobile application executor engine 202, a hotspot screener 204, a preview of initial stage application performance health component 206, a deep dive analysis component 208, and a reporting library 210 that is in communication with a dashboard 212.

A device integration bridge library works in conjunction with a framework of mobile application performance component 200, receiving inputs that include an APK/IPA file, build version, environmental conditions and automation scripts for execution. In some embodiments, a bot based execution is carried out using AI trained bots, and the above inputs are fed to the bot for execution. In some embodiments, an intelligent bot identifies which test cases are to be executed first. For example, the intelligent bot may decide under which environmental condition(s) the application needs to be tested, etc. In some embodiments the intelligent bot derives these use cases in reference to the available historical data. For example, a benchmark library 214 may provide benchmark information to a key performance indicator (KPI) analyzer 216 that may determine correlations between timing of events in the application, network, and resource KPIs. Application responsiveness may be determined, as well as network and resource utilization.

For example, the intelligent bot may not only prioritize the test cases and environment, but it may also identify the performance hotspots 250 and bottlenecks via various log files. In some embodiments, the KPIs measured are compared against an industry standard (e.g., using benchmark library 214), and the performance targets agreed in a statement of work (SOW) document. In some embodiments, the intelligent performance bot may provide (206) a score card 232 on the application performance and may provide recommendations towards remediation of performance issues. In some embodiments, a bug tracker 234 may be provided. In some embodiments, mobile application performance component 200 may perform the following:

(1) Application build review—To validate whether best practices are being applied when packaging the application (e.g., compression, proguard, cyclometric complexity). Examples of tools that may be used include Sonarqube and the software development kit (SDK) tools of the device.

(2) Resource measurements—CPU, GPU, Memory, Battery, Storage—To validate whether the application uses resources optimally. Examples of tools that may be used include Gamebench, Trepn Profilers and SDK profilers.

(3) Network analysis—To validate whether the application responds under set service level agreements (SLAs) for mobile network conditions (e.g., 3G/4G).

(4) Worst case analysis—To validate whether the application responds well when having multiple applications/processes running in the background and when resource availability is constrained (e.g., to determine application performance when the device battery power is at 10%, or when CPU utilization is 95%).

(5) Performance code profiling—Method/Render/Memory profiling.

For example, deep dive analysis 208 may include a CPU/Battery profiler 218, a memory profiler 220, a method profiler 222, and a network profiler 224. In some embodiments, CPU/Battery profiler may determine usage of wake locks 260. In some embodiments, memory profiler 220 may determine memory intensive objects 262. In some embodiments, method profiler 222 may determine top time consuming methods 264, and network profiler 224 may determine resource usage associated with API calls, and response sizes 266.

In some embodiments, logs on the device record timestamps and corresponding system events. For example, the logs may be used to determine timing of page loads (e.g., to determine that transitioning from a display of a first page to a display of a second page took 6 seconds), as well as identifying what code or routines were being used to perform the page loads. Thus, an optimizer may be informed of performance issues, and of what portions of code may be responsible for the performance issues.

In some embodiments, deep dive analysis 208 may provide, to reporting library 210, actionable insights 226, a periodical/trend view 228, and a build comparison 230, which may be used by dashboard 212 to provide analysis results and/or recommendations to a user (e.g., via a display device).

Figure 3A:
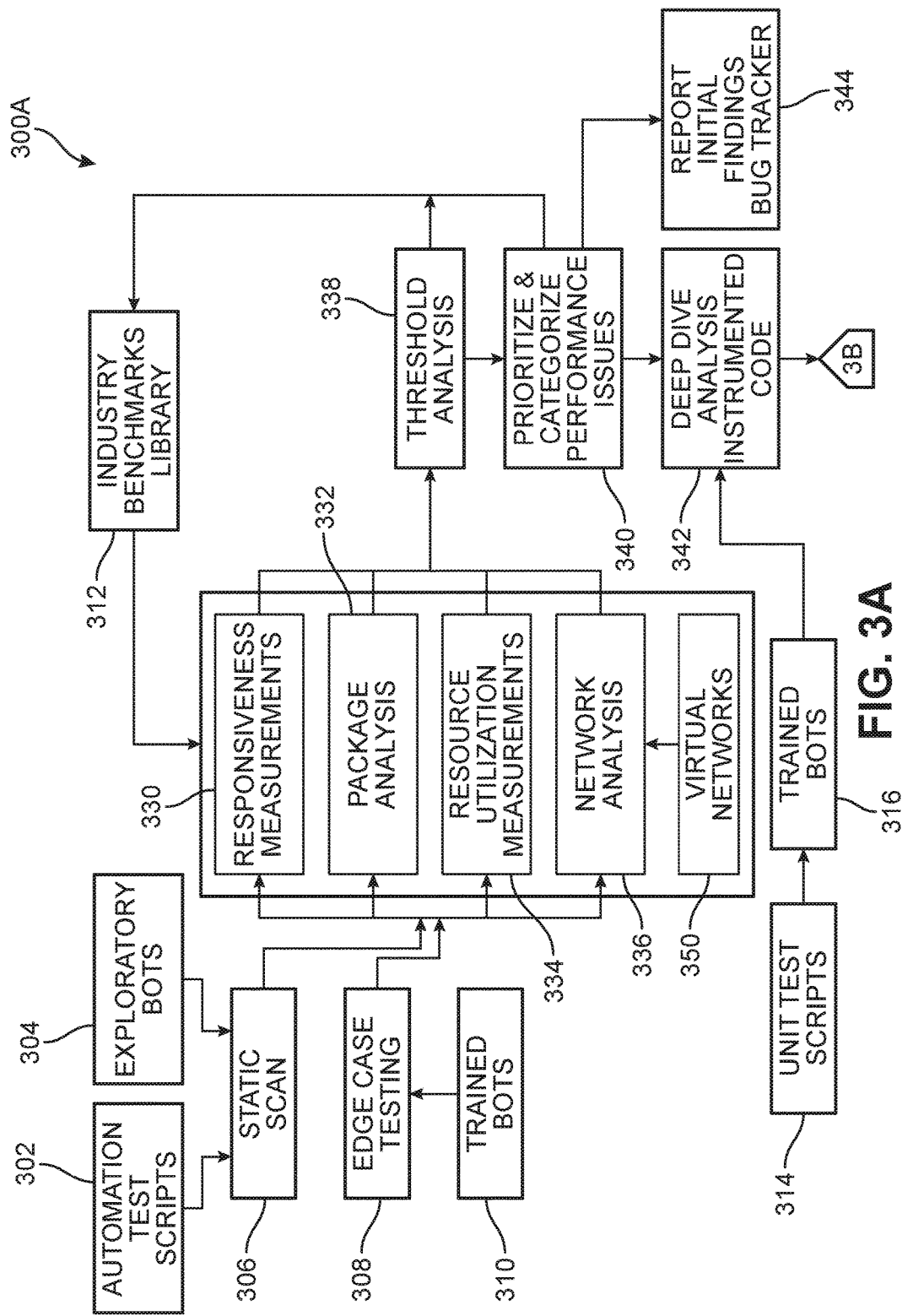
FIGS. 3A-3B are a schematic diagram of a system for controlling quality of performance of a digital application.
Figure 3B:
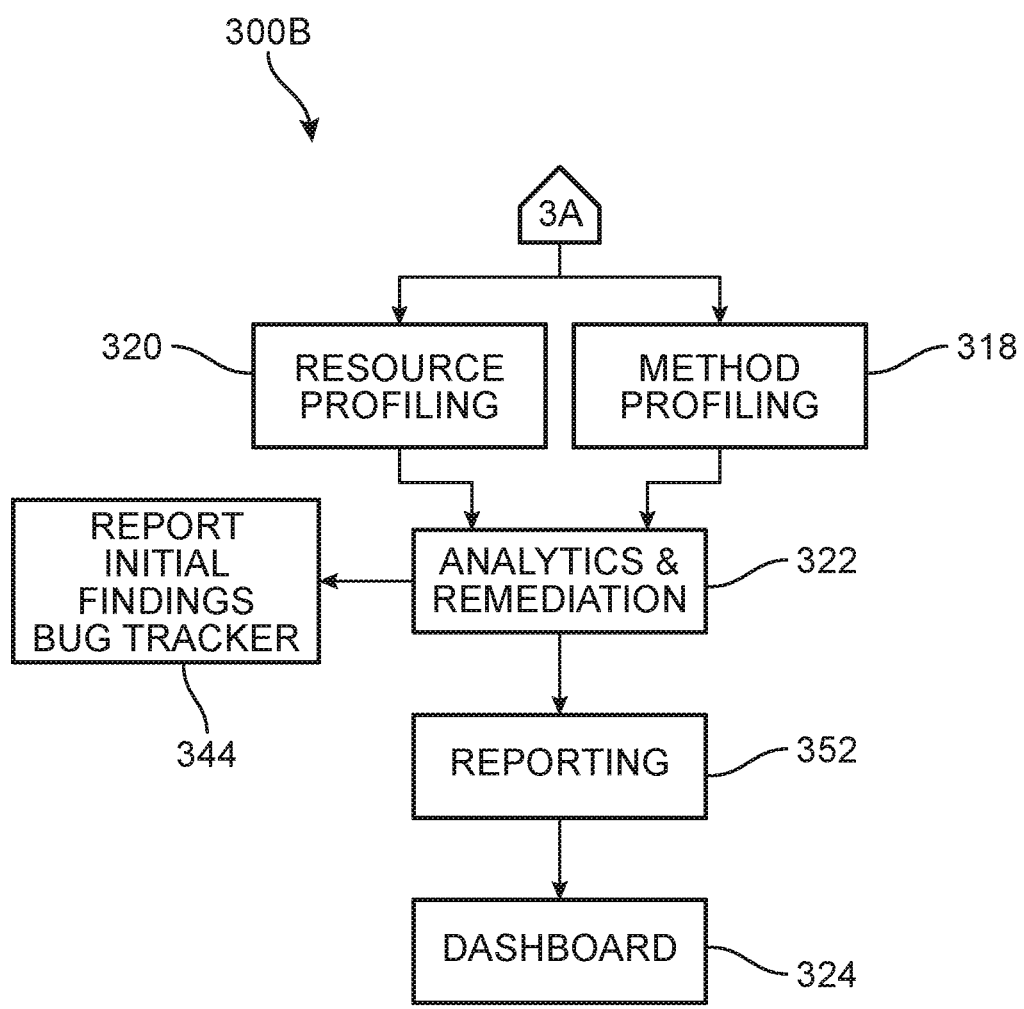

FIGS. 3A-3B are a schematic diagram of an embodiment 300A, 300B for controlling quality of performance of a digital application using bot driven performance diagnostics. As shown in FIG. 3A, a static scan 306 may be performed using automation test scripts 302 and exploratory bots 304. In some embodiments, exploratory bots 304 may use machine learning (ML) to accurately define user flows by learning from other contemporary applications. As shown in FIG. 3A, edge case testing 308 may be performed using trained bots 310. For example, trained bots 310 may utilize algorithms to perform randomized and repeatable tasks for testing, and may use machine learning (ML) to define user flows by learning from other contemporary applications.

An industry benchmarks library 312 may be utilized in conjunction with responsiveness measurements 330, a package analysis 332, resource utilization measurements 334, and a network analysis 336, which may include an analysis of virtual networks 350, to provide a threshold analysis 338, which may then be used to prioritize and categorize performance issues 340, as discussed above. Initial findings may be reported, and bugs may be tracked 344. In some embodiments, machine learning may be used to determine combinations of input data that may qualify as performance risks. In some embodiments, unit test scripts 314 and trained bots 316 may be used to perform a deep dive analysis via instrumented code 342. For example, deep dive analysis 342 may include profilers as discussed above with regard to deep dive analysis 208 as discussed above. For example, the code may be obtained from a code repository (e.g., a user's play store) for testing and instrumentation. In some embodiments, unit test scripts 314 may use unit test cases that are correlated with end user flows. In some embodiments, trained bots 316 may perform unit level tests on the problematic user flows that are identified.

In some embodiments, "bots" (or "monkey bots") may include automated agents/scripts that may perform interactions on mobile apps and web applications. Such bots may be substantially unregulated execution agents that perform erratic actions on the application to understand failure points (e.g., non-standard user flows). For example, these actions may include actions that intended to stress the application, such as infinite scrolling, repeated button clicks, misplaced button clicks, constant page refreshes.

In some embodiments, "trained bots" may include automated agents/scripts that perform specific interactions pertaining to the domain of the application (retail/hospitality/finance, etc.). For example, such bots may be trained with historical data to perform specified transactional activities pertaining to the domain.

In some embodiments, unit test scripts and trained bots may be configured to perform the analysis via instrumented code, for example, by labelling the trained bots against the corresponding unit test scripts. For example, trained bots may execute specific unit test scripts pertaining to the area of code that the system identified in the earlier block (as part of issue containerization) and generate performance data that is then compared with the earlier performance runs.

In some embodiments, a role of the "machine learning" discussed above may include recognizing app screens and application flows based on successful executions by bots (e.g., monkey bots) and these flows may be validated against manual test cases to ensure correctness and completeness, and these flows may aid in building the industry specific automation library. Another example role may include defining and refining the threshold of performance benchmarks for various performance metrics and heuristics related to response time measurements, package optimization, resource utilization measurements and network usage. Yet another example role may include issue containerization and predicting point of failures and potentially identifying root causes based on correlated analysis of performance and industry benchmarks.

In some embodiments, using unit test scripts 314 that are correlated with end user flows may include careful documentation of traceability between end user flows. For example, tags may used to tag each transaction of an end user journey to a specific unit test case.

In some embodiments, as shown in FIG. 3B, method profiling 318 and/or resource profiling 320 may be performed. For example, method profiling 318 may consider a method timing hierarchy, function call timings, call stack, locks, and waits. For example, resource profiling 320 may consider possible performance issues associated with memory leaks and garbage collection. Resource profiling 320 may include CPU usage analysis, memory profiling, identifying classes, and functions that consume resources.

In some embodiments, analytics and remediation 322 may be provided automatically to reporting 352, and a unified dashboard 324 may be used to provide the user with unified reports that identify possible performance issues, as well as provide recommendations for remediation of the performance issues and/or potential performance issues (and/or provide notification that immediate fixes have been automatically performed).

Figure 4:
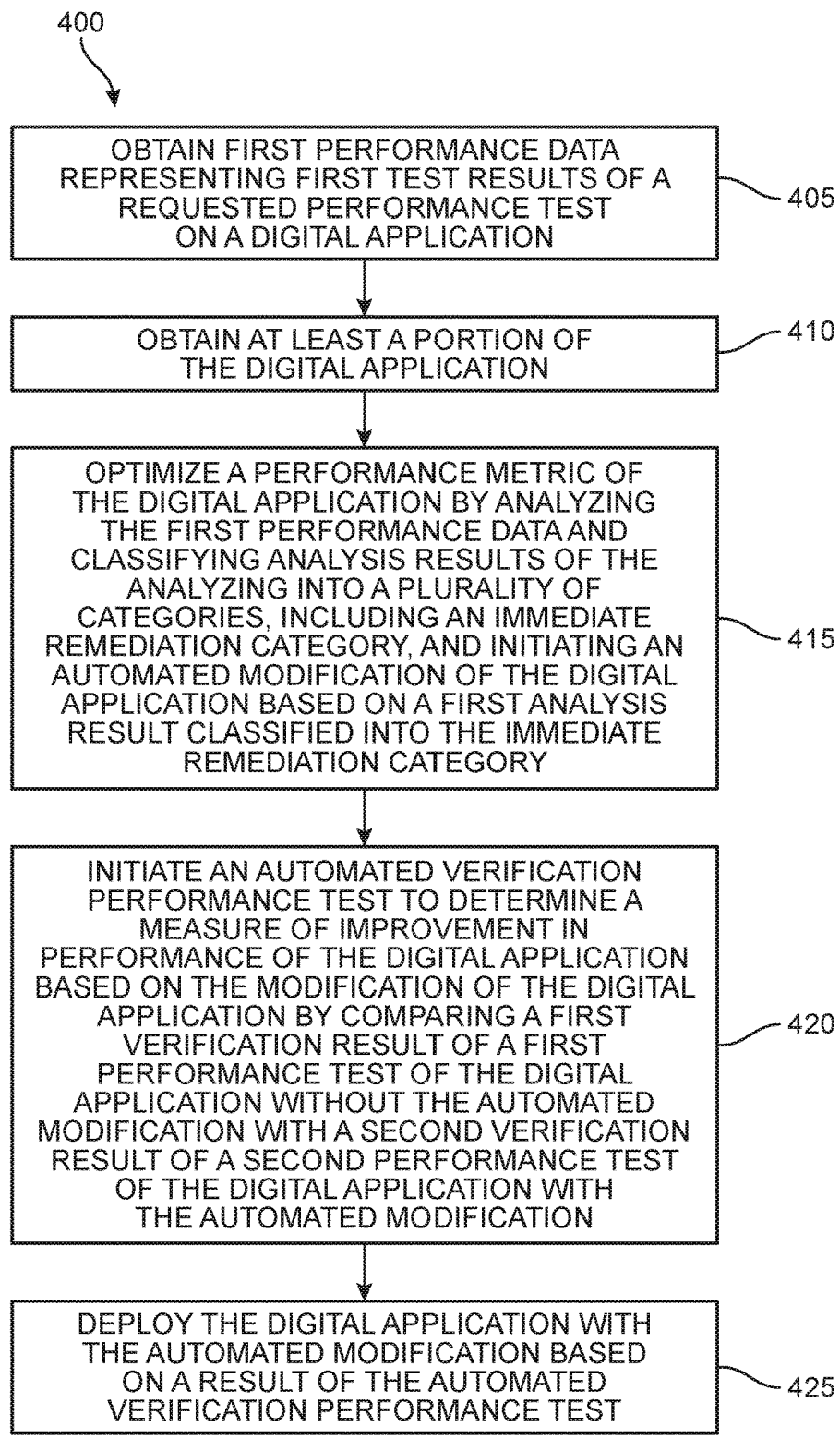
FIG. 4 is a flowchart of an embodiment of controlling quality of performance of a digital application.

FIG. 4 is a flowchart 400 of an example embodiment of controlling quality of performance of a digital application. As shown in FIG. 4, in step 405, first performance data may be obtained representing first test results of a requested performance test on the digital application. In step 410, at least a portion of the digital application may be obtained. In step 415, a performance metric of the digital application may be optimized by analyzing the first performance data and classifying analysis results of the analyzing into a plurality of categories, the plurality of categories including an immediate remediation category, and initiating an automated modification of the digital application based on a first analysis result classified into the immediate remediation category. In step 420, an automated verification performance test may be initiated to determine a measure of improvement in performance of the digital application based on the modification of the digital application by comparing a first verification result of a first performance test of the digital application without the automated modification, with a second verification result of a second performance test of the digital application with the automated front end modification. In step 425, the digital application with the automated modification may be deployed based on a result of the automated verification performance test.

Example techniques discussed herein may advantageously automate the entirety of controlling quality of performance of digital applications, for both web or mobile applications. For example, the holistic solution may provide advantageous performance improvement in a dev-ops scenario that may involve rapid delivery and may be time-bound.

Implementations of the various techniques described herein may be implemented in digital electronic circuitry, or in computer hardware, firmware, software, or in combinations of them (e.g., an apparatus configured to execute instructions to perform various functionality).

Alternatively, implementations may be implemented as a computer program embodied in a machine usable or machine readable storage device (e.g., a magnetic or digital medium such as a Universal Serial Bus (USB) storage device, a tape, hard disk drive, compact disk, digital video disk (DVD), etc.), for execution by, or to control the operation of, data processing apparatus, e.g., a programmable processor, a computer, or multiple computers. Such implementations may be referred to herein as implemented via a non-transitory "computer-readable storage medium" or a "computer-readable storage device."

A computer program, such as the computer program(s) described above, can be written in any form of programming language, including compiled, interpreted, or machine languages, and can be deployed in any form, including as a stand-alone program or as a module, component, subroutine, or other unit suitable for use in a computing environment. The computer program may be tangibly embodied as executable code (e.g., executable instructions) on a machine usable or machine readable storage device (e.g., a computer-readable medium). A computer program that might implement the techniques discussed above may be deployed to be executed on one computer or on multiple computers at one site or distributed across multiple sites and interconnected by a communication network.

Method steps may be performed by one or more programmable processors executing a computer program to perform functions by operating on input data and generating output. The one or more programmable processors may execute instructions in parallel, and/or may be arranged in a distributed configuration for distributed processing. Example functionality discussed herein may also be performed by, and an apparatus may be implemented, at least in part, as one or more hardware logic components. For example, and without limitation, illustrative types of hardware logic components that may be used may include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Processors suitable for the execution of a computer program include, by way of example, both general and special purpose microprocessors, and any one or more processors of any kind of digital computer. Generally, a processor may receive instructions and data from a read only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory may be supplemented by, or incorporated in special purpose logic circuitry.

To provide for interaction with a user, implementations may be implemented on a computer having a display device, e.g., a cathode ray tube (CRT), liquid crystal display (LCD), or plasma monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback. For example, output may be provided via any form of sensory output, including (but not limited to) visual output (e.g., visual gestures, video output), audio output (e.g., voice, device sounds), tactile output (e.g., touch, device movement), temperature, odor, etc.

Further, input from the user can be received in any form, including acoustic, speech, or tactile input. For example, input may be received from the user via any form of sensory input, including (but not limited to) visual input (e.g., gestures, video input), audio input (e.g., voice, device sounds), tactile input (e.g., touch, device movement), temperature, odor, etc.

Further, a natural user interface (NUI) may be used to interface with a user. In this context, a "NUI" may refer to any interface technology that enables a user to interact with a device in a "natural" manner, free from artificial constraints imposed by input devices such as mice, keyboards, remote controls, and the like.

Examples of NUI techniques may include those relying on speech recognition, touch and stylus recognition, gesture recognition both on a screen and adjacent to the screen, air gestures, head and eye tracking, voice and speech, vision, touch, gestures, and machine intelligence. Example NUI technologies may include, but are not limited to, touch sensitive displays, voice and speech recognition, intention and goal understanding, motion gesture detection using depth cameras (e.g., stereoscopic camera systems, infrared camera systems, RGB (red, green, blue) camera systems and combinations of these), motion gesture detection using accelerometers/gyroscopes, facial recognition, 3D displays, head, eye, and gaze tracking, immersive augmented reality and virtual reality systems, all of which may provide a more natural interface, and technologies for sensing brain activity using electric field sensing electrodes (e.g., electroencephalography (EEG) and related techniques).

Implementations may be implemented in a computing system that includes a back end component, e.g., as a data server, or that includes a middleware component, e.g., an application server, or that includes a front end component, e.g., a client computer having a graphical user interface or a Web browser through which a user can interact with an implementation, or any combination of such back end, middleware, or front end components. Components may be interconnected by any form or medium of digital data communication, e.g., a communication network. Examples of communication networks include a local area network (LAN) and a wide area network (WAN), e.g., the Internet.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

We claim:

1. A method of controlling quality of performance of a digital application, the method comprising:
   obtaining first performance data representing first test results of a requested performance test on the digital application;
   obtaining at least a portion of the digital application;
   optimizing a performance metric of the digital application by:
      analyzing the first performance data and classifying analysis results of the analyzing into a plurality of categories, the plurality of categories including an immediate remediation category for recommended modifications that can be performed automatically and a short term remediation category including design modifications associated with a design of the digital application, and initiating an automated modification of the digital application based on a first analysis result classified into the immediate remediation category;

initiating an automated verification performance test to determine a measure of improvement in performance of the digital application based on the modification of the digital application by comparing a first verification result of a first performance test of the digital application without the automated modification with a second verification result of a second performance test of the digital application with the automated modification; and deploying the digital application with the automated modification based on a result of the automated verification performance test.

2. The method of claim 1, wherein the digital application includes a web application.

3. The method of claim 1, wherein the digital application includes a mobile application configured to reside on a mobile device.

4. The method of claim 1, wherein analyzing the first performance data includes comparing the first performance data to a threshold performance benchmark that is based on at least one of historical benchmark data and competitive benchmark data.

5. The method of claim 1, wherein the plurality of categories includes a long term remediation category, wherein long term remediation includes one or more modifications of methodology associated with a development phase of the digital application.

6. The method of claim 1, wherein obtaining the first performance data includes initiating the requested performance test on the digital application via one or more of:
on-demand testing,
scheduled testing, or
periodic monitoring of the digital application.

7. The method of claim 1, wherein obtaining the first performance data includes initiating the requested performance test on the digital application using trained bots that are trained using a machine learning algorithm.

8. The method of claim 1, wherein obtaining the first performance data includes initiating the requested performance test on the digital application using simulated operating conditions of execution, including one or more of simulated network conditions, simulated CPU conditions, or simulated memory conditions.

9. The method of claim 1, wherein obtaining the first performance data includes obtaining log data from one or more logs on a device executing the requested performance test on the digital application, the logs storing at least timestamp data and associated execution events that occur on the device.

10. The method of claim 1, wherein initiating the automated modification of the digital application based on the first analysis result classified into the immediate remediation category includes initiating an automated optimization of the digital application based on one or more of:
modifying code for image compression,
modifying code for textual compression,
removing unused code in the digital application,
modifying code to optimize front end loading of the digital application,
modifying code to optimize runtime JavaScript performance, or
modifying code to request pre-loading of download items.

11. A non-transitory computer-readable medium storing software comprising instructions that are executable by one or more device processors to control quality of performance of a digital application by:
obtaining first performance data representing first test results of a requested performance test on the digital application;
obtaining at least a portion of the digital application;
optimizing a performance metric of the digital application by:
analyzing the first performance data and classifying analysis results of the analyzing into a plurality of categories, the plurality of categories including an immediate remediation category for recommended modifications that can be performed automatically and a short term remediation category including design modifications associated with a design of the digital application, and
initiating an automated modification of the digital application based on a first analysis result classified into the immediate remediation category;
initiating an automated verification performance test to determine a measure of improvement in performance of the digital application based on the modification of the digital application by comparing a first performance test of the digital application without the automated modification with a second performance test of the digital application with the automated modification; and
deploying the digital application with the automated modification based on a result of the automated verification performance test.

12. The non-transitory computer-readable medium of claim 11, wherein analyzing the first performance data includes comparing the first performance data to a threshold performance benchmark that is based on at least one of historical benchmark data and competitive benchmark data.

13. The non-transitory computer-readable medium of claim 11, wherein the plurality of categories includes a long term remediation category, wherein long term remediation includes one or more modifications of methodology associated with a development phase of the digital application.

14. The non-transitory computer-readable medium of claim 11, wherein obtaining the first performance data includes initiating the requested performance test on the digital application via one or more of:
on-demand testing,
scheduled testing, or
periodic monitoring of the digital application.

15. The non-transitory computer-readable medium of claim 11, wherein obtaining the first performance data includes initiating the requested performance test on the digital application using trained bots that are trained using a machine learning algorithm.

16. The non-transitory computer-readable medium of claim 11, wherein obtaining the first performance data includes initiating the requested performance test on the digital application using one or more simulated operating conditions of execution, including simulated network conditions, simulated CPU conditions, or simulated memory conditions.

17. The non-transitory computer-readable medium of claim 11, wherein obtaining the first performance data includes obtaining log data from one or more logs on a device executing the requested performance test on the digital application, the logs storing at least timestamp data and associated execution events that occur on the device.

18. The non-transitory computer-readable medium of claim 11, wherein initiating the automated modification of the digital application based on the first analysis result classified into the immediate remediation category includes initiating an automated optimization of the digital application based on one or more of:
- modifying code for image compression,
- modifying code for textual compression,
- removing unused code in the digital application,
- modifying code to optimize front loading of the digital application,
- modifying code to optimize runtime JavaScript performance, or
- modifying code to request pre-loading of download items.

19. A system for controlling quality of performance of a digital application, the system comprising:
- a device processor; and
- a non-transitory computer readable medium storing instructions that are executable by the device processor to:
  - obtain first performance data representing first test results of a requested performance test on the digital application;
  - obtain at least a portion of the digital application;
  - optimize a performance metric of the digital application by:
    - analyzing the first performance data and classifying analysis results of the analyzing into a plurality of categories, the plurality of categories including an immediate remediation category for recommended modifications that can be performed automatically and a short term remediation category including design modifications associated with a design of the digital application, and
    - initiating an automated modification of the digital application based on a first analysis result classified into the immediate remediation category;
  - initiate an automated verification performance test to determine a measure of improvement in performance of the digital application based on the modification of the digital application by comparing a first verification result of a first performance test of the digital application without the automated modification with a second verification result of a second performance test of the digital application with the automated modification; and
  - deploy the digital application with the automated modification based on a result of the automated verification performance test.

20. The system of claim 19, wherein initiating the automated modification of the digital application based on the first analysis result classified into the immediate remediation category includes initiating an automated optimization of the digital application based on one or more of:
- modifying code for image compression,
- modifying code for textual compression,
- removing unused code in the digital application,
- modifying code to optimize front loading of the digital application,
- modifying code to optimize runtime JavaScript performance, or
- modifying code to request pre-loading of download items.

* * * * *